United States Patent [19]
Hettinger, Jr.

[11] 3,975,516
[45] Aug. 17, 1976

[54] METHODS OF TREATING CELLULAR TISSUE

[76] Inventor: William P. Hettinger, Jr., 37 St. Andrews Road, Severna Park, Md. 21146

[22] Filed: June 5, 1972

[21] Appl. No.: 259,556

Related U.S. Application Data

[63] Continuation-in-part of Ser. No. 881,616, Dec. 2, 1969, abandoned.

[52] U.S. Cl. .............................................. 424/81
[51] Int. Cl.² ........................................ A61K 31/78
[58] Field of Search ..................................... 424/81

[56] References Cited
OTHER PUBLICATIONS

Drugs vs. Cancer, National Cancer Inst., Research Report, HEW, 1968, pp. 1 and 3.

Wichterler et al., Nature, Jan. 9, 1960, pp. 117–118.

*Primary Examiner*—Jerome D. Goldberg
*Attorney, Agent, or Firm*—Buell, Blenko & Ziesenheim

[57] ABSTRACT

A process is provided for encasement and infiltration of cellular tissue to reduce the influx of oxygen and liquid thereto and to retain in situ and retard efflux of liquids and medication therefrom by introducing into said tissue a gel substantially insoluble in said tissue and the body fluids associated therewith.

1 Claim, No Drawings

METHODS OF TREATING CELLULAR TISSUE

This application is a continuation-in-part of my co-pending application Ser. No. 881,616, filed Dec. 2, 1969, now abandoned.

This invention relates to methods of treating cellular tissue and particularly to a tissue treatment based upon the encasement of or infiltration by a gel of tissue so as to provide an impervious mass or barrier layer and/or so as to locally fix anti-tumor chemicals, or tumorangiogenesis factor and/or to reduce or eliminate the influx of oxygen, nutrients and critical amino acids and thus cut off and control or at least retard tissue growth. It is generally known that there are physical conditions involving relatively rapidly moving cell growth, e.g., carcinomas, and other tumors and there have been many attempts made to retard or prevent this growth without any real success. I have discovered that it is possible to encase or fill living tissue, such as cancerous tissue, with an impervious barrier material which will retain or localize chemotherapeutic agents or tumorangiogenesis factor and/or reduce or eliminate the influx of essential oxygen, nutrients and critical amino acids upon which the cell tissue grows and thrives. This may be accomplished in several ways as, for example, by injecting into the area to be isolated separate solutions of monomer and catalyst which are brought together as they enter the area to be isolated and immediately gel, blocking off and isolating the area. Alternatively, the monomer and gelation agent may be combined and injected at an appropriate time prior to complete gelation or the gel may be formed and injected into the tissue to be treated. The injection may be by way of a high pressure atomizing gun, hypodermic needle or by any of a variety of other methods which will be obvious to men who are skilled in the art of introducing into body tissue various treating agents. It is also possible to inject polymer forming monomer and catalyst into the blood stream adjacent to the area to be isolated along with the necessary catalyst so as to substantially block the capillary system which normally feeds the cellular tissue. In this practice the monomer would be injected into the arterial side of the blood supply to the area so as to stop or block critical capillary flow and extra cellular plasma flow. In cases where the lymphatic system is involved, a similar injection into the lymph, upstream of drainage flow may similarly be employed. For example, the polymerizable fluid is injected into a lymph system to which a metastasis of a tumor has occurred. The lymph involvement could be located in any area of the body, the polymerizable fluid being injected upstream of the section involved into the lymph system so that the involved lymph and associated glands are invaded with the polymerizable gel.

In the practice of my method, I may also apply an encapsulating, immobilizing or non-penetrating substance into the cancerous or other cellular tissue which material is readily polymerized and I can add, or simultaneously add, a therapeutic agent or a material which will precipitate as an insoluble organic or inorganic substance. The readily polymerized substance may be acrylamide, N, N$^1$ methylenebisacrylamide or any like readily polymerizable substance. Preferably, water soluble polymers having a molecular weight greater than 10,000 or polymers cross linked so as to be insoluble are used. The insolubilizing substance can also preferably be a high molecular weight poly carboxylic acid or poly amino polymeric substance. The therapeutic agent may be any material which is desired to be slow released into the tissue for treatment or control of growth. For example, the gel, e.g., poly acrylamide, may be used as a barrier for tumor-angiogenesis factors, or a carrier for estrogens, androgens, Cytoxan (cyclophosphamide), Mustargen (mechlorethamine); Oncovin (Vincristine); Thio TEPA (triethylenethiophosphoramide); Methotrexate (4-amino-N-10 methylpteroylglutamic acid); Dactinomycin (Actinomycin-D); Leuperan (Chlorambucil); (4- p-[Bis (2 chlorethyl) amino] phenyl butyric acid) Prednisone; (17, 21-dihydroxy pregna -1,4 diene-3, 11, 20 trione); Hydrocortisone (Cortisol); Velbon; Vinblastine (vinaleukoblastine); HN$_2$ and other chemotherapeutic agents. Broadly stated, I provide a process for encasement and infiltration of cellular tissue to reduce the influx of oxygen and liquids thereto, to reduce the efflux of tumor angiogenesis factors and to retain in situ and retard efflux of anticarcinogenic agents comprising the steps of introducing into said tissue a gel either as an inorganic or an organic material in the form of a polymer gel, or an organic material capable of forming a gel by polymerization and polymerizing said material just prior to or just after injection into said tissue.

The invention can perhaps best be understood by reference to the following examples.

EXAMPLE I

A gel system is made by dissolving 20 grams of AM-9 (acrylamide powder containing N, N$^1$ methylenebisacrylamide as a cross linking agent) and 3.5 ml of DMAPN (dimethylaminopropionitrile) in 25.5 ml of H$_2$O, a catalyst solution is made by dissolving 1 gram of AP (ammonium persulfate) in 50 ml H$_2$O. The time of gelation of this mixture when introduced into a cell structure is about 7 seconds. The system when injected into a cell system by first injecting the catalyst followed by the monomer solution promptly gelled and closed off entry into the system by other liquids and by air.

EXAMPLE II

A first solution is made up of 5 grams of AM-9 3.5 ml of DMAPN (dimethylaminopropionitrile) and 40 ml of water. A second solution is made up of 50 ml H$_2$O, and 1 gram of AP (ammonium persulfate). The solutions are introduced into separate hypodermic needles and injected together into a body cell structure of a rat. The gel time in the cell structure is about 20 seconds. The material was tested on rodents and the acute oral dosage for rodents was found to be 200 mg per kg or the equivalent of 10 grams per 100 lbs. of body weight. The recovery from contact with the material is slow but effective.

EXAMPLE III

In situ polymerization was achieved by perfusing a dilute solution of monomer (AM-9) through the tissue to be treated, while simultaneously subjecting the critical tissue to high energy irradiation.

EXAMPLE IV

A 1 percent solution of polyacrylic acid was made slightly acidic with hydrochloric acid until the viscosity was sufficiently reduced so as to permit injection. Upon injection the pH of the solution increased rapidly, and gelation occurred within the cell structure.

EXAMPLE V

One hundred fifty rats were tested for toxicity of acrylamide by injecting acrylamide polymer (7 percent by weight) into cell tissue areas on the back of the rats. No toxicity indications appeared in any of the treated rats.

EXAMPLE VI

Sheets of endothelial cells were exposed in a culture of the acrylamide polymer solution of Example V for 6 days. At the end of this period the cell tissue was healthy and went through active mytosis when stimulated.

EXAMPLE VII

A group of rats with large Walker 256 carcinosarcomas was injected with the acrylamide polymer of Example V and the polymer gelled in the tissue forming an encapsulation in the area of injection.

EXAMPLE VIII

A group of rats with large B 16 melanomas was treated as in Example VII with like results.

EXAMPLE IX

A group of rabbits with Brown-Pierce epithaliomas (carcinoma) were treated using the acrylamide polymer of Example V injected into the anterior chamber of the eye. Here again the gel formed within the cell structure of the tissue.

The various gel formers which appear to be satisfactory for gelation or polymerization in the tissue include: acrylic acid; methacrylic acid; acrylamide; N, $N^1$-methylenebisacrylamide; N-dimethyl ethylacrylate; acrolein; polycarboxylic acid; polyacrylic acid; polymethacrylic acid; ethylene-maleic acid copolymer; divinyl ether-maleic anhydride copolymer; polyvinyl-sulfonic acid; polystyrene parasulfonic acid; N-diemthylaminoethylacrylate; N dimethylaminoethyl methacrylate; diacetone acrylamide; methylolacrylamide; amino-ethylmeth-acrylate; as well as those monomers set out at pages 411–455 of the *Journal of Polymer Science*, Vol. 54 (1961). All of these monomers are well known and their copolymer forms closely predictable.

Other methods of application may be visualized by one skilled in the art, and the above examples should in no way be construed as limiting the method of application. Any of the monomer systems outlined above, either alone or with others may be used along with suitable catalytic systems including the oxygen supply of the blood in the treated area.

While I have generally described certain preferred practices of my invention in the foregoing general description and specification, it will be understood that this invention may be otherwise embodied within the scope of the following claims.

I claim:

1. A process for encasement and infiltration of animal cellular tissue to reduce the influx of oxygen nutrients, amino acids and liquids thereto, to reduce the efflux of liquids therefrom and to retain in situ and retard efflux of liquids and therapeutic agents and to block capillary and extra cellular plasma flow, comprising the steps of introducing into said animal tissue an effective amount of a polyacrylamide gel substantially insoluble in said animal tissue and body fluids associated therewith.

* * * * *